United States Patent [19]

Mann

[11] Patent Number: 5,282,973
[45] Date of Patent: Feb. 1, 1994

[54] METHOD FOR CHARGING AND DISCHARGING CHROMATOGRAPHY COLUMN BED

[75] Inventor: William H. Mann, Chattanooga, Tenn.

[73] Assignee: Chromaflow, Inc., Chattanooga, Tenn.

[21] Appl. No.: 5,551

[22] Filed: Jan. 19, 1993

Related U.S. Application Data

[62] Division of Ser. No. 742,592, Aug. 8, 1991, Pat. No. 5,213,683.

[51] Int. Cl.$^5$ .............................. B01D 15/08
[52] U.S. Cl. .................. 210/656; 210/198.2; 95/82; 96/101
[58] Field of Search .............. 95/82; 96/101; 210/656, 210/659, 198.2, 189, 268, 270, 289, 291; 141/12, 80

[56] References Cited

U.S. PATENT DOCUMENTS

| | | | |
|---|---|---|---|
| 2,597,693 | 5/1952 | Wolcott | 210/270 |
| 2,773,612 | 12/1956 | Penick | 210/268 |
| 2,781,301 | 2/1957 | Payne | 210/268 |
| 3,200,067 | 8/1965 | Levendusky | 210/268 |
| 3,424,674 | 1/1969 | Webber | 210/270 |
| 3,512,639 | 5/1970 | Kugelman | 210/268 |
| 3,966,609 | 6/1976 | Godbille | 210/198.2 |
| 4,079,009 | 3/1978 | Seiler | 210/198.2 |
| 4,597,866 | 7/1986 | Couillard | 210/198.2 |
| 4,743,373 | 5/1988 | Rai | 210/198.2 |
| 4,769,141 | 9/1988 | Couillard | 210/198.2 |
| 4,891,133 | 1/1990 | Colvin | 210/198.2 |
| 4,894,152 | 1/1990 | Colvin | 210/198.2 |
| 5,021,162 | 6/1991 | Sakamoto | 210/198.2 |
| 5,141,635 | 8/1992 | LePlang | 210/198.2 |

FOREIGN PATENT DOCUMENTS

| | | | |
|---|---|---|---|
| 105583 | 4/1984 | European Pat. Off. | 210/198.2 |
| 61-294361 | 12/1986 | Japan | 210/198.2 |

*Primary Examiner*—Ernest G. Therkorn
*Attorney, Agent, or Firm*—Alan Ruderman

[57] ABSTRACT

A chromatography column having a media supply and product/buffer inlet assembly positioned at the inlet of a dispersion section at the top of the column and an outlet assembly positioned at the collection section at the bottom of the column for receiving and discharging product components and buffer liquid and for discharging liquefied spent media. The media and product inlet assembly includes a housing having a product and buffer inlet passage including a selectively movable media supply nozzle extending through the housing. The nozzle may be positioned through the dispersion section into the column housing for spraying media in the form of a slurry into the column housing, and may be withdrawn after the media bed is packed. The collection section of the column includes a hollow rod extending through a discharge conduit through which spent media may flow. The rod has a probe at the upper end for entering into the column, a point at the end of the probe being adapted to puncture and chip spent hardened media. Buffer liquid is pumped through the rod and out apertures in the probe to loosen and liquefy the spent media which thereafter flows through the discharge conduit. Spent media may thus be removed from the column and the column recharged with fresh media without disassembly of the column.

2 Claims, 2 Drawing Sheets

METHOD FOR CHARGING AND DISCHARGING CHROMATOGRAPHY COLUMN BED

This application is a division, of application Ser. No. 07/742,592, filed Aug. 8, 1991, now U.S. Pat. No. 5,213,683.

BACKGROUND OF THE INVENTION

This invention relates to a liquid chromatography column and more particularly to the removal of the spent media bed from and the charging of a fresh media bed into a chromatography column without disassembling the column.

Chromatography is a process of separation of the components of a mixture of chemical substances. The separation occurs by percolation of fluid through a body or bed of comminuted or porous rigid material, the various components being resolved by their selective retardation as they are transported through the bed by a moving fluid or buffer. A solution of the substances to be separated becomes the moving phase of the system passing through the interstices in the stationary or continuous phase which are finely divided particles in the form of a gel or slurry. The substances in the moving phase is poured into the top of a chromatography column filled with the finely divided material, i.e., the media, that can absorb differentially the substances to be separated. The particular material used for the media varies widely with the substances to be separated. As the solution percolates down the column the components are separated from the buffer fluid which generally is pumped back into the top of the column so as to again pass down through the bed as a carrier. The different substances as they travel down the column at different rates form bands of the different substances which are individually collected at the outlet.

As aforesaid the media of the continuous phase is a very fine particulate slurry or gel initially, but after it has been used for sometime it hardens and loses its effectiveness and becomes a dense mass. This spent media must then be removed from the column and replaced in the column with a fresh supply, i.e., the column must be repacked.

A chromatography column comprises a hollow vertically disposed cylindrical housing including a liquid dispensing section at the upper end and through which the buffer and substances to be separated are dispensed to the media bed, and a liquid collecting section at the lower end for collecting the substances and buffer individually. The media or bed through which the buffer fluid and mixture to be separated and purified percolates is located between these sections. The liquid dispensing section and liquid collecting section each include a respective plate and at least one, and generally both, of the plates are connected in an assembly with an axially movable plunger-like body positioned within the housing at the respective end. After the column is charged with the bed media the bodies are forced relatively to each other to compress and pressurize the media bed which has been poured into the column.

The known prior art methods for packing the bed of small diameter columns used for research and development, e.g., only a few inches in diameter, are fully disclosed in Sakamoto et al U.S. Pat. No. 5,021,162 dated Jun. 4, 1991. In the conventional liquid flow method applicable to columns of larger diameter used in production of useful products such as synthetic insulin, e.g., approximately two feet in diameter, the bed media slurry is poured into a reservoir which has been temporarily connected to the upper end of the chromatography column. The reservoir is then closed at the top and liquid is pumped under pressure through the reservoir and the column. Excess liquid floating above the bed is pumped from the reservoir and the reservoir is then removed. This leaves part of the bed over-flowing above the top of the column, and the column is closed after this excess bed media is removed. In that method, as with most of the other prior art proposals discussed in the aforesaid patent, the top of the column must be disconnected in order to charge or pack the bed and must then thereafter be reassembled.

As aforesaid, after the column has been in use for a time, the fine particle slurry gradually hardens into a dense mass. When this occurs the bed loses its effectiveness and thereafter must be removed from the column. The removal of spent slurry in the prior art requires that the bottom of the column be opened and that the plunger-like assemblies be disconnected from the cylindrical housing. Thereafter the hardened slurry dense mass must be broken up by chopping and the like and removed from the column. The time required to remove this spent slurry, the reassembly of the bottom plunger-like assembly to the housing, the recharging of the housing and the reassembly of the top plunger-like assembly is relatively substantial. In fact, the life of the bed during separation and purification production runs may be no greater than the maintenance time required for the removal of the spent bed and the recharging of the column. Clearly, if less time is required to remove the spent slurry and recharge the column, production costs for the process may be substantially reduced.

SUMMARY OF THE INVENTION

Accordingly, it is a primary object of the present invention to provide a method and apparatus for substantially reducing the amount of time for charging the bed media of a chromatography column and for removing the media after it is spent.

It is another object of the present invention to provide a method and apparatus which permits removal of spent slurry or bed media from a chromatography column and recharging of the column with fresh slurry without disassembling the column.

It is a further object of the present invention to provide a chromatography column having a packing valve assembly for charging the column with bed media and a dump valve assembly for removing spent bed media, without requiring the column to be disassembled.

Accordingly, the present invention provides a chromatography column having a media and product inlet assembly positioned at the inlet of the plunger-like assembly at the top of the column, the media and product inlet assembly including a housing having a product-/buffer inlet passage including a movable media supply nozzle extending through the housing in sealed relationship with the product/buffer inlet passage, the nozzle being selectively positioned through the dispersion section including the dispersion plate for spraying slurry into the column, and being withdrawn after the bed is packed. Additionally, and significantly, the invention further provides a chromatography column with a dump valve assembly at the plunger-like assembly at the bottom of the column, the dump valve assembly including a hollow rod extending concentrically through a discharge conduit through which spent media may flow, the rod being selectively movable through the collector section including the collector plate and into the column, and having a probe at the upper end for puncturing and chipping the spent hardened media. Liquid, such as the buffer liquid, may be pumped through the hollow of the rod and out apertures in the probe to loosen and liquefy the spent media which thereafter flows through the discharge conduit. Preferably the media discharge conduit is concentrically disposed within the product and buffer discharge passage at the outlet of the collector plate.

BRIEF DESCRIPTION OF THE DRAWINGS

The particular features and advantages of the invention as well as other objects will become apparent from the following description taken in connection with the accompanying drawings in which.

DESCRIPTION OF THE PREFERRED EMBODIMENT

Figure 1:
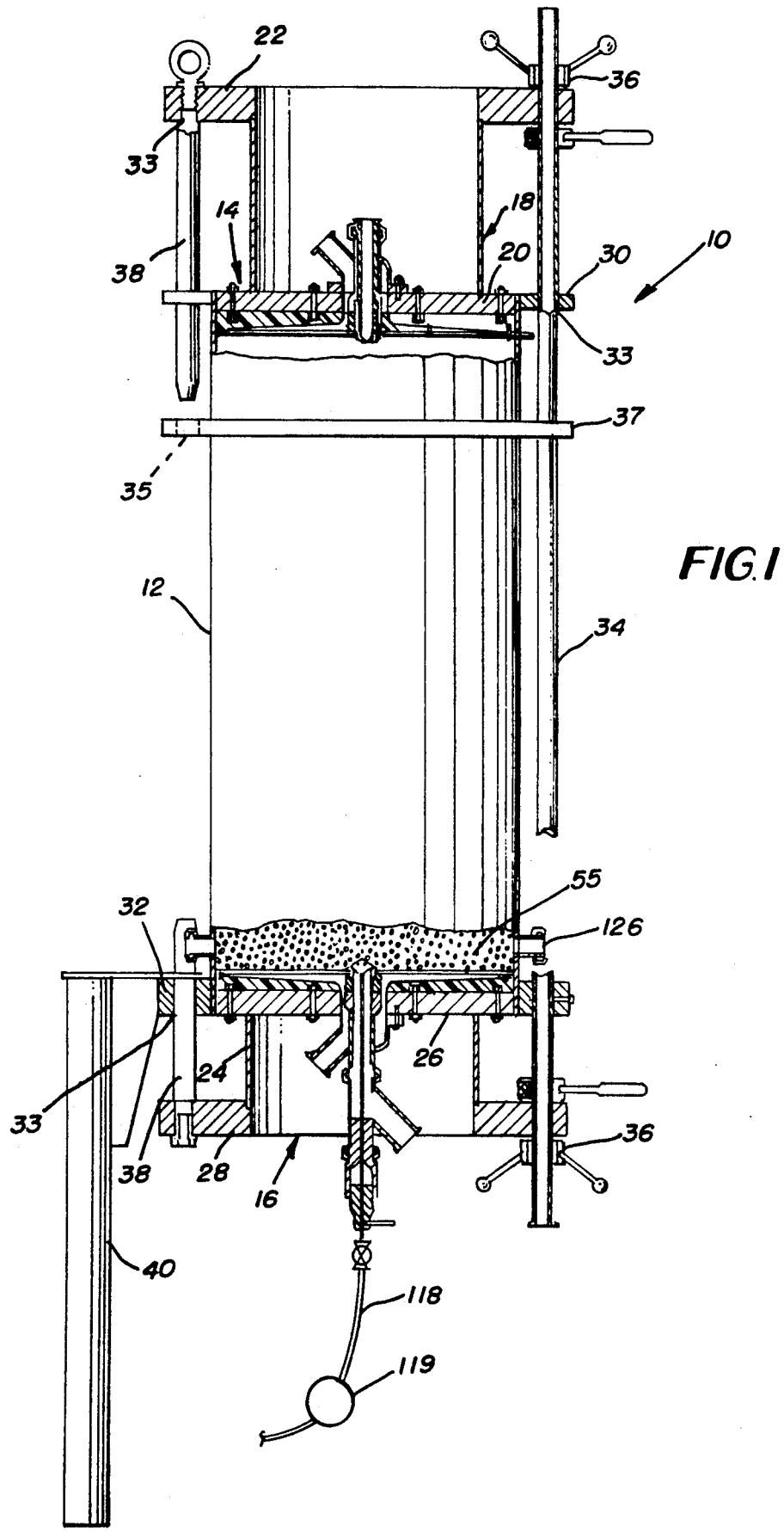
FIG. 1 is an elevational view, partly in cross section of a chromatography column including apparatus constructed in accordance with the present invention.

Referring to the drawings, FIG. 1 illustrates a chromatography column 10 having apparatus constructed in accordance with the principles of the present invention. The column 10 comprises an elongated hollow cylindrical housing 12 having a dispersion section 14 at the top and a collecting section 16 at the bottom, the housing preferably being constructed from stainless steel. The dispersion section 14 includes a hollow cylindrical elongated drum 18 having an upper cylindrical plunger head 20 formed at the lower end and a flange 22 formed at the top, the head 20 normally being disposed within the upper portion of the housing 12. The drum 18, plunger 20 and flange 22 also preferably are constructed from stainless steel and the plunger head and flange preferably are welded to the central drum 18. Likewise, the collection section 16 comprises a hollow cylindrical drum 24 having a lower cylindrical plunger head 26 and a flange 28 welded thereto, the plunger head 26 being disposed within the lower portion of the housing. The column housing 12 includes an upper and lower ring or flange 30, 32 respectively welded thereto, the flanges 22, 28, 30 and 32 having a series of circumferentially spaced apart and aligned bores such as 33 for receiving a series of securing rods 34, only one of which is illustrated. The rods 34 have tightening members such as nuts or the like 36 threaded thereon at the remote top and bottom surfaces of the flanges 30 and 32 so as to draw the flanges 22 and 28 toward the column and thus move the plunger heads into the housing. Another flange 37 may also be welded to the column housing and has bores 35 through which the rods 36 are also received. Other rod members 38 receivable in certain of the bores may serve as legs for the dispensing and collecting section drums 18, 24 when disassembled from the column and act as guide rods when the drums are to be assembled to the column. Three or more legs 40, only one of which is illustrated, are welded to the flange 32 for positioning the column above the floor upon which it is mounted.

Figure 2:
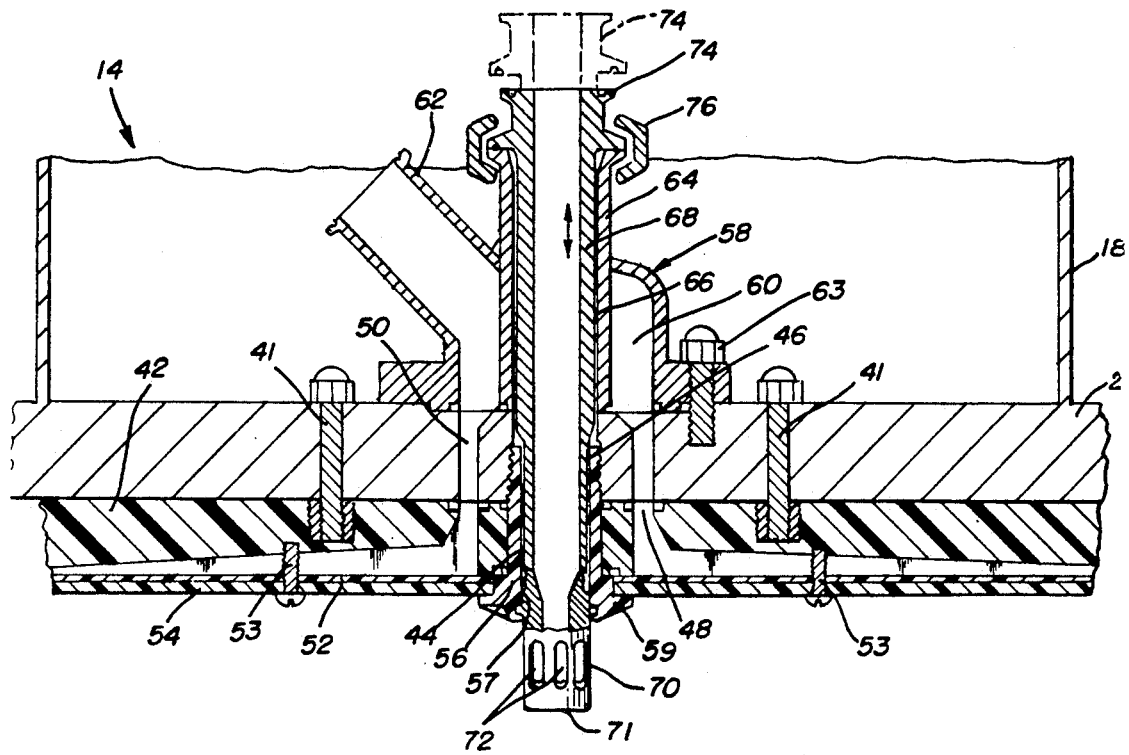
FIG. 2 is an enlarged fragmentary cross sectional view of the dispersion section of the chromatography column illustrated in FIG. 1.

The details of the dispersing section may be understood with reference to FIG. 2. Thus, supported from the upper plunger head 20 by means of a plurality of bolts or screw members or the like 41 is a dispersion plate 42, the plate preferably being constructed from polypropylene or similar material. The dispersion plate 42 comprises a disk having a plurality of radially extending spaced apart ribs (not illustrated) disposed on the surface remote from the plunger head 20, i.e., the lower surface, and includes a central bore 44 which is aligned with a central bore 46 in the plunger head 20. A plurality of approximately 12 holes 48 are disposed in the plate 42 between the ribs spaced radially from the bore 44, while a similar series of holes 50 are disposed in the plunger head 20 spaced radially from the bore 46 and aligned with the holes 48. Fastened to the underside of the dispersion plate is a perforated plastic support grid 52 which supports a sintered polyethylene filter 54, the support grid 52 and filter 54 being carried by the dispersion plate by means of screws 53 threaded into spaced apart ribs in the dispersion plate 42. Thus, as known in the art, the product and buffer liquid fed to the upper plunger head 20 flows through the holes 50 and 48 into the passages of the dispersion plate between the ribs, and is dispersed substantially uniformly onto the grid 52 and then onto the filter 54 where it is filtered and flows down into the media 55 in the housing 12. The grid 52 and filter 54 each have central bores aligned with the bore 44 of the plate 42 and a plastic annular nut 56 having a central bore 57 is received therethrough and threaded into the plunger head 20, an enlarged head 59 of the nut abutting the filter 54 to aid in securement of the members.

In accordance with one aspect of the present invention, an inlet manifold housing 58 comprising a casting or welded assembly including an inverted cup-shape cavity 60 having a product and buffer inlet conduit 62 extending at an angle to the cavity 60 and opening therein, is secured to the upper surface of the plunger head 20 by screws 63 or the like. The inlet manifold housing 58 includes a centrally disposed nozzle receiving tube 64 having an internal bore 66 aligned with and opening onto the bore 46 of the plunger head 20. Disposed within the bore 66 of the tube 64 is an elongated hollow spray nozzle body 68 having a nozzle head 70 at the lower end 71 and comprising a plurality of oval shaped apertures 72 disposed about the periphery and having the lower end closed, the upper end 74 of the nozzle body being connected to a slurry media supply line (not illustrated).

The nozzle is received through the central bore 57 of the securing nut 56, and in the media packing position, illustrated in FIG. 2 extends below the head 59 into the housing 12. In this position the nozzle body 68 is clamped to the upper end of the nozzle receiving tube 64 by a clamp such as a compressible keyhole shaped clamp or the like 76. The media in the form of a slurry or gel may then be pumped through the nozzle into the housing 12. Prior to the separation and purification run the clamp 76 is loosened and the nozzle body 68 is drawn upwardly until the surface of the lower end 71 of the nozzle body is at substantially the same level as the opening in the nut 56. At this location the bore 57 is sealed and the nozzle body is again clamped. The separation and purification run may then be commenced by feeding product and buffer liquid through the inlet conduit 62.

The collection section 16 is similar to the dispersion section 14 except that the order of parts is reversed. The lower plunger head 26 supports a collection plate 78 bolted thereto, the collection plate being substantially identical to the dispersion plate 42 and carries a support grid 80 and a filter 82 which are secured thereto in the same manner as those elements in the dispersion section, the grid 80 and filter 82 being substantially identical to those elements in the dispersion section. Additionally, the collection section has an outlet manifold 84 substantially identical to the inlet manifold 58 including an outlet conduit 86 and a centrally disposed tube 88 having an internal bore 90 aligned with and opening onto bores in the plunger head 26 and the collection plate 78. Here, separated material which has been separated in the media of the column housing 12 flows onto the filter 82, through the grid 80 and onto the surface of the collection plate 78. The ribs of the plate guide the separated and purified material toward holes 92 disposed radially about the central bore and through holes 94 in the plunger head 26 similar to the holes 50 in the plunger head 20 of the dispersion section. This material then flows out the conduit 86 to a three-way valve (not illustrated) to product collector vessels or the like. After the product has been removed, the buffer liquid travels the identical path except that the three-way valve directs it to piping and back to the inlet conduit 62.

Clamped by clamping means 96 to the tube 88 at the lower end is another tube 98 having an outlet conduit 100 disposed angularly relatively thereto. The interior of the lower end of the main portion of the tube 98 receives a rod support body 102, the tube 98 and the body 102 having external flange portions clamped together by clamping means 104. The rod support body has a hollow interior including an enlarged internally threaded bore at the lower end for threadedly receiving an externally threaded plug member 106, the plug 106 having a central bore which receives and is secured to a hollow elongated rod 108 by means of a set screw or the like 109. The interior hollow of the rod 108 defines a flow passage 107 for reasons which will hereinafter become clear. A manually engagable handle 110 is also secured to the plug member 106 for rotating the member 106 to drive it further into or out of the rod support body 102. As illustrated the rod 108 extends upwardly through the tubes 98 and 88, the latter preferably having a guide ring 111 therein, and has a probe 112 with a substantially pointed tip at the upper end. The probe 112 includes a plurality of spray apertures 114 communicating with the flow passage 107 of the interior of the rod 108. The lower end of the rod is connected to valve means 116 and to a feed line 118 which is attached to a quick disconnect arrangement (not illustrated) to the buffer liquid supply pump 119. The periphery of the probe 112 is substantially the same size as the bore of a nut 120 which is substantially identical to the nut 56 in the dispersion section, the nut 120 extending through the collection plate, the grid and the filter and being threaded into the plunger housing 26.

Figure 3:
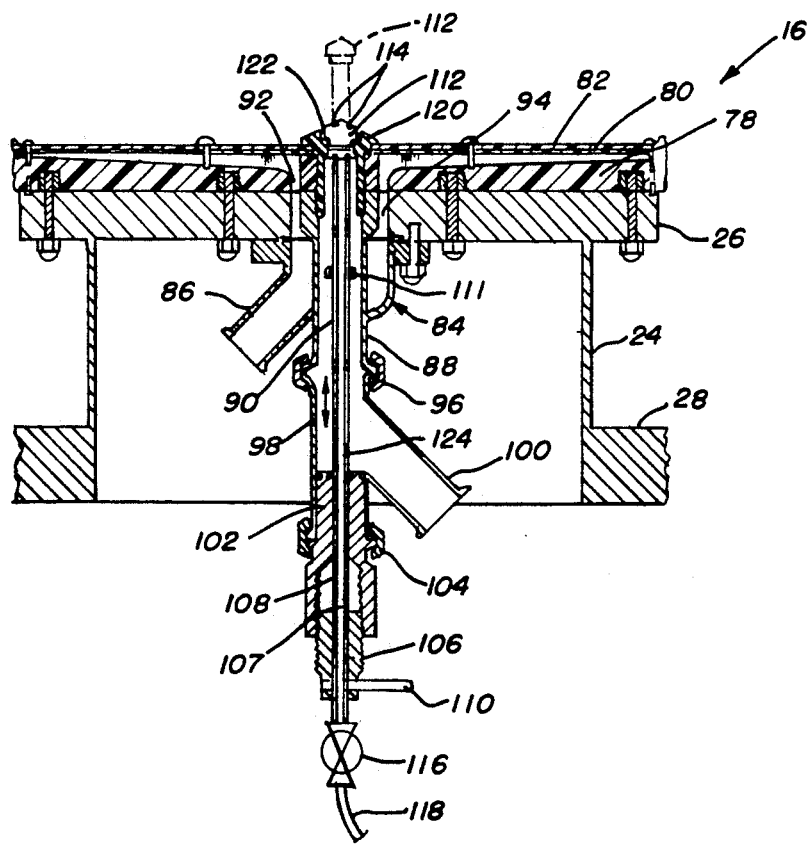
FIG. 3 is an enlarged fragmentary cross sectional view of the collection section of the column illustrated in FIG. 1.

During the separation run as aforesaid, the product and the buffer liquid are separately removed through the outlet tube 86. During this period the probe is sealed by a gasket 122 within the securing nut 120 which there acts as a probe sealing member so that all of the product and buffer flows through the filter 82, and through the holes 94 in the plate 78 and out the conduit 86. After the media 55 has been used for a period of time and becomes spent, the plug 106 is rotated by means of the handle 110 to drive the rod 108 upwardly so as to drive the probe 112 into the housing 12. If the media has solidified the pointed probe will puncture and chip it as the probe forcibly enters the housing. The feed line 118 is then connected to the buffer supply which is fed from the pump 119 under high pressure through the flow passage 107 of the rod 108 and sprayed through the apertures 114 into the housing 12 to liquefy the hardened media. As the media liquefies it can flow through the central opening in the nut 122, around the rod 108 and out the conduit 100 as it is precluded by the rod support body 102 from flowing down in the direction toward the plug 106. After the media has been removed, the rod 108 is lowered to the housing closing position, illustrated in FIG. 3, the line 118 being disconnected by the quick disconnect means. The housing 12 is then ready to be refilled with fresh media.

The rod 108 may have a plurality of venturi openings such as that illustrated at 124 at longitudinally spaced locations so that as the buffer flows through the rod a suction is created to aid in drawing the liquefied spent media through the tubes 88 and 98 from the housing 12. Additionally, if found necessary, buffer inlet ports 126 may be included at lower peripheral portions of the housing 12 so as to permit buffer under pressure to be fed directly into the housing to aid in the media removal process.

Accordingly, the present invention provides apparatus and a method for removing spent media from the housing of a chromatography column and to recharge the column with fresh media without necessitating disassembly of the column. When fresh media is supplied to the chromatography column the nuts 36 which are threaded onto the securing rods 34 are loosened so that the upper plunger head 20 and the elements attached thereto may freely float until the media has attained the desired level. The nuts 36 are then retightened to compress the media slurry as aforesaid. No disassembly of the chromatography column, however, is required.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A method for replacing the media bed in a chromatography column through which a mixture to be separated into component substances and a buffer liquid may percolate from a dispensing section to a collection section without requiring disassembly of said column, said method comprising opening a port in the collection section to communicate the interior of said column with a media outlet conduit, driving a movable probe through said port and into the column to puncture and chip hardened media, pumping fluid through said probe into said column to loosen and liquefy said media so that said media may flow through said port to said outlet conduit, and filling said column with fresh media at the dispersion section.

2. The method as recited in claim 1, wherein said filling of said media comprises opening a portal in the dispersion section, inserting a movable nozzle through said portal and into said column, and feeding media through said nozzle to fill said column.

* * * * *